(12) United States Patent
Sweeny et al.

(10) Patent No.: US 8,329,105 B1
(45) Date of Patent: Dec. 11, 2012

(54) PORTABLE FURNACE FOR ASSAYING A CRUSHED ORE SAMPLE

(76) Inventors: Richard E. Sweeny, Denver, CO (US); William B. Lewelling, Lakewood, CO (US)

( * ) Notice: Subject to any disclaimer, the term of this patent is extended or adjusted under 35 U.S.C. 154(b) by 997 days.

(21) Appl. No.: 12/321,423

(22) Filed: Jan. 20, 2009

(51) Int. Cl.
*G01N 31/12* (2006.01)
(52) U.S. Cl. ............ 422/78; 422/557; 432/156; 432/159
(58) Field of Classification Search .................. 266/271; 422/78; 373/137; 432/156
See application file for complete search history.

(56) References Cited

U.S. PATENT DOCUMENTS 220,895 A * 10/1879 Wight ............................ 432/159

* cited by examiner

*Primary Examiner* — Jill Warden
*Assistant Examiner* — Julie Tavares
(74) *Attorney, Agent, or Firm* — Edwin H. Crabtree; Ramon L. Pizarro

(57) ABSTRACT

A lightweight, compact, easy-to-use, portable furnace used for quickly assaying crushed ore samples in the field and used by prospectors, miners, and geologists. The portable furnace can also be used for smelting precious metals and refining and recycling different metals. The furnace includes a metal stand having a stand base with a first end portion with a dish opening therein and a second end portion with an upwardly folded heat shield. The heat shield includes a nozzle groove therein for receiving a gas nozzle. The gas nozzle is part of a gas blow torch having a handle and a gas tank. The stand base also includes first and second sides folded downwardly for holding the metal stand above a flat surface. A bottom of a scorifying dish is received in the dish opening. A cupel is received inside the open top of the scorifying dish. The cupel is adapted for receiving a crushed ore sample therein to be assayed. A dish lid is received on top of the scorifying dish. The lid is used to help direct a gas flame from the end of the gas nozzle around the outer circumference of the cupel and heating and assaying the ore sample inside the cupel.

17 Claims, 2 Drawing Sheets

PORTABLE FURNACE FOR ASSAYING A CRUSHED ORE SAMPLE

BACKGROUND OF THE INVENTION (a) Field of the Invention

This invention relates to a portable furnace for assaying ore samples and more particularly, but not by way of limitation, to a light weight, portable furnace using a gas blow torch for heating a crushed ore sample inside a cupel and assaying the sample in the field or laboratory for a rare metal.

(b) Discussion of Prior Art

Heretofore, prospectors and miners have faced a problem of positively identifying an amount or a type of rare metal in a rock specimen. Two methods have been used to test rock specimens in the field. They are chemical tests and fire tests. Chemical tests involve the use of acids and reagents to cause a color change or other reaction in hope of revealing the contents in the specimen. Within the area of chemical tests are leaching tests, which mimic the last stages of gold mining on a small scale to produce a pure metal extract. Fire tests involve heating the rock specimen with a flame to produce a color change, sublimation, or other effect, which gives a clue to the contents in the specimen.

The tests mentioned above are attempts to answer the "What is it?" question, know as a qualitative test, and the "How much is there?" question, known as a quantitative test. Until now, only the above mentioned leach test can answer both of these questions in the field.

While the above testing methods have proven effective over the years, they require bulky, heavy and fragile equipment and knowledge of chemistry. Inclement weather and remote, rough terrain can make the use of this equipment in the field difficult. Therefore, prospectors, miners and geologists have resorted to taking rock samples to laboratories for assaying. The transporting of the samples involves transportation costs, added labor and time wasted, which can be used more profitably in the field.

Also, while a laboratory assay can be a reliable method to answer the qualitative and quantitative questions, it is expensive and time consuming. Further, the cost of a furnace capable of smelting and refining ore samples is prohibitive for an individual miner or prospector. Although there are small, table top furnaces available on the market, they require electrical power or natural gas, which limits their use to the laboratory. Also, their weight further prohibits these types of furnaces in the field.

In an attempt to solve the above assaying of ore sample problems in the field, some assay operators use small portable oxygen/acetylene gas welding equipment along with a cupel or crucible. The major problem with this approach is the time involved. These type of assays often take more than an hour to perform and operator fatigue becomes a factor long before the process is complete.

The subject invention provides a unique portable, light weight furnace for assaying different types of rare metal ore samples in the field and eliminating the need of the above mentioned assaying equipment.

SUMMARY OF THE INVENTION

In view of the foregoing, it is a primary objective of the subject invention to provide a lightweight, compact, easy-to-use, portable furnace for quickly assaying crushed ore samples in the field. The portable furnace can be used by prospectors, miners, and geologists to determine initially if a mining prospect should be claimed and developed.

Another object of the invention is the portable furnace can be also used for smelting precious metals and refining and recycling different metals.

Still another object of using the portable furnace is to eliminate wasted time, labor and expense in shipping samples to an assay laboratory. Also the handling of heavy, bulky assay equipment in the field is eliminated.

The subject invention includes a metal stand having a stand base with a first end portion with a dish opening therein and a second end portion with an upwardly folded heat shield. The heat shield includes a nozzle groove therein for receiving a gas nozzle. The gas nozzle is part of a gas blow torch having a handle and a gas tank. The stand base also includes first and second sides folded downwardly for holding the metal stand above a flat surface. A bottom of a scorifying dish is received in the dish opening. A cupel is received inside the open top of the scorifying dish. The cupel is adapted for receiving a crushed ore sample therein to be assayed. A dish lid is received on top of the scorifying dish. The lid is used to help direct a gas flame from the end of the gas nozzle around the outer circumference of the cupel and heating and assaying the ore sample inside the cupel.

These and other objects of the present invention will become apparent to those familiar with various types of assay equipment for assaying ore samples when reviewing the following detailed description, showing novel construction, combination, and elements as herein described, and more particularly defined by the claims, it being understood that changes in the embodiments to the herein disclosed invention are meant to be included as coming within the scope of the claims, except insofar as they may be precluded by the prior art.

BRIEF DESCRIPTION OF THE DRAWINGS

The accompanying drawings illustrate complete preferred embodiments in the present invention according to the best modes presently devised for the practical application of the principles thereof, and in which.

DETAILED DESCRIPTION OF THE PREFERRED EMBODIMENTS

Figure 1:
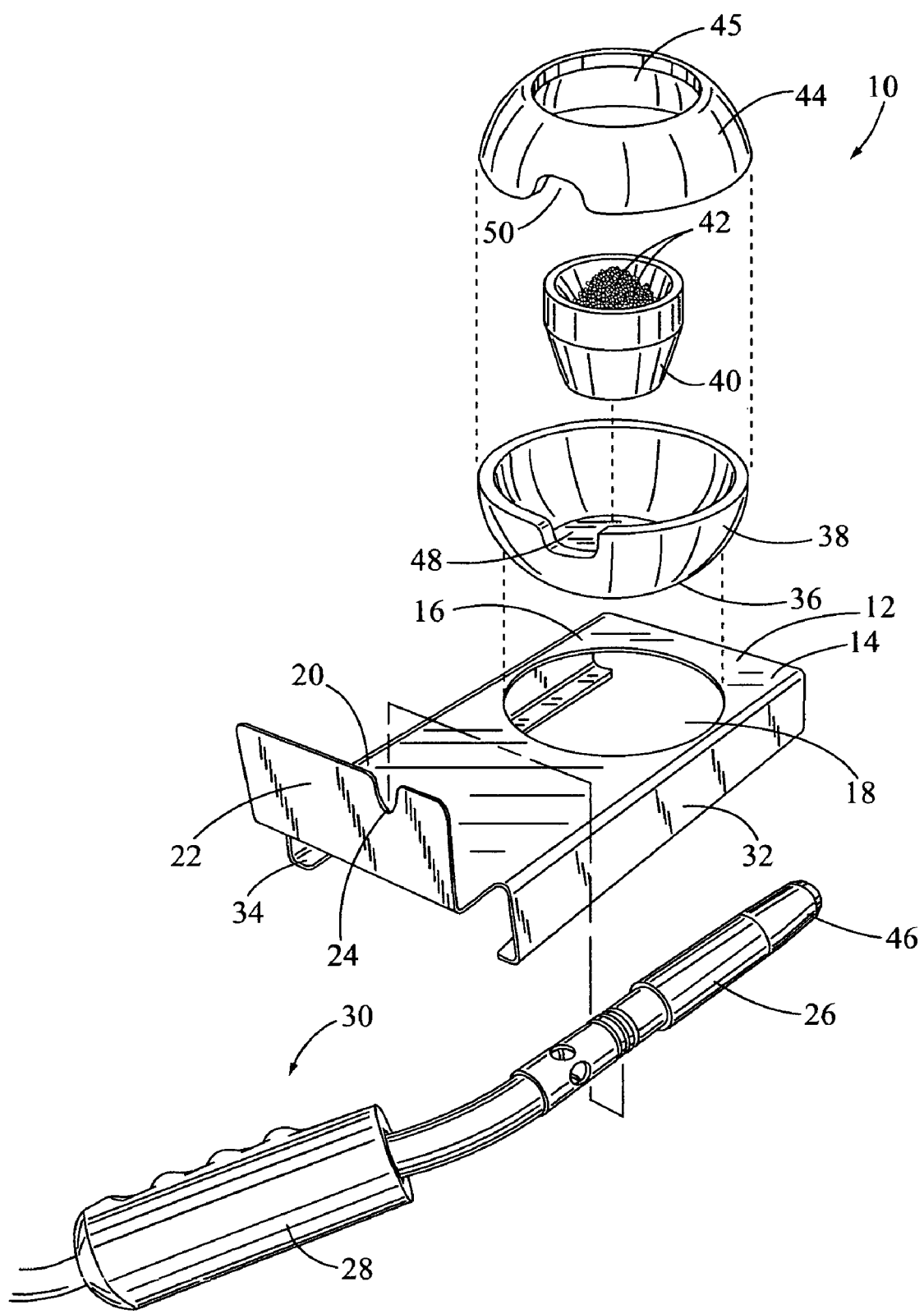
FIG. 1 is an exploded, perspective view of a primary embodiment of the portable furnace and illustrating a metal stand, a scorifying dish, a cupel with crushed ore sample, a dish lid with opening in the top thereof and gas nozzle with handle, which is part of a gas blow torch.

In FIG. 1, an exploded, perspective view of the subject portable furnace is shown and having general reference numeral 10. The furnace 10 includes a metal stand 12 having a stand base 14. The stand base 14 includes a first end portion 16 with a dish opening 18 therein and a second end portion 20 with an upwardly folded heat shield 22. The heat shield 22 includes a nozzle groove 24 therein for receiving a gas nozzle 26 attached to a handle 28. The gas nozzle 26 and handle 28 are part of a gas blow torch, having a general reference numeral 30. The gas blow torch 30 includes a gas tank, which is not shown in the drawings. The stand base 14 also includes first side 32 and a second side 34. The sides 32 and 34 are folded downwardly and vertically for holding the metal stand 12 above a flat surface, such as a table top or ground surface.

A bottom 36 of a scorifying dish 38 is received in the dish opening 18. A cupel 40 is received inside the open top of the scorifying dish 38. The cupel 40 is adapted for receiving a crushed ore sample 42 therein to be assayed. A dish lid 44, with an open top 45, is received on top of the scorifying dish 38 and covering the cupel 40 received thereon. The lid 44 is used to help direct a gas flame from an end of the gas nozzle 26 around an outer circumference of the cupel 40 and out the open top for heating and assaying the ore sample 42 inside the cupel. It should be noted that dish 38 includes a dish groove 48 and the lid 44 includes a lid groove 50. The two grooves 48 and 50 are used for receipt around a portion of the end 46 of the gas nozzle 26 for holding the end 46 in place as the flame from the nozzle is directed around the outside of the cupel 40.

Figure 2:
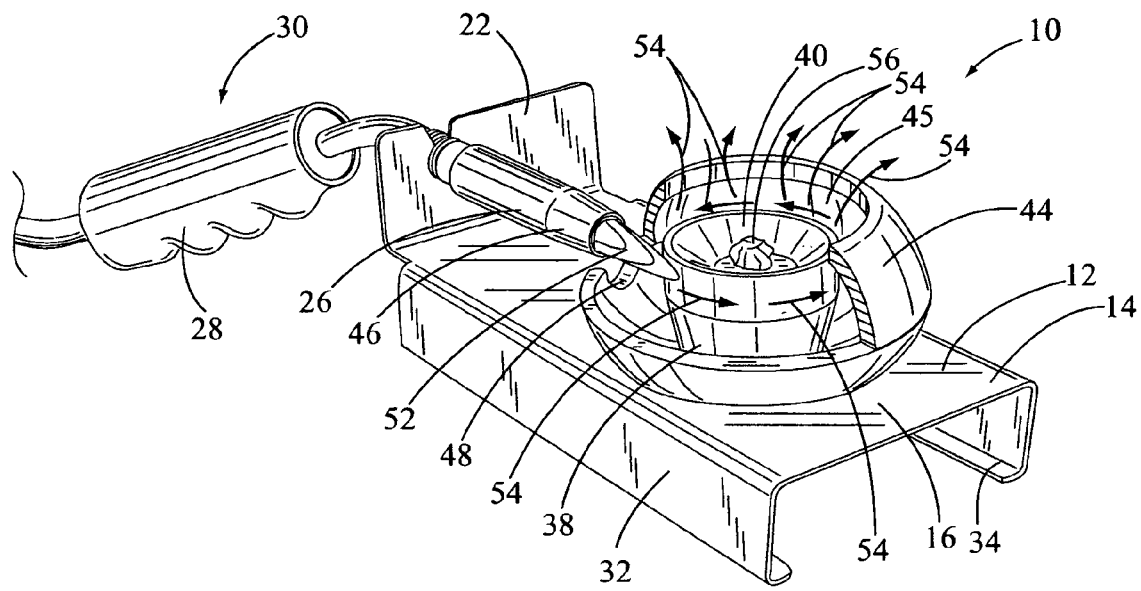
FIG. 2 is a perspective view of the portable furnace shown in FIG. 1 and with the end of the gas nozzle received inside the scorifying dish and lid with a flame and heated gas circulated around an outer circumference of the cupel for heating the crushed ore.

In FIG. 2, a perspective view of the portable furnace 10 is shown in operation. In this drawing a part of the dish lid 44 has been cut away. A gas flame 52 from the end 46 of the gas nozzle 26 is shown received inside the scorifying dish 38 and dish lid 44. Heated gas, shown as arrows 54 from the flame 52 is circulated around an outer circumference of the cupel 40 for heating the crushed ore. The end of the nozzle 26 is offset in the dish groove 48 and the lid groove 50 so that the flame 52 contacts tangentially the side of the cupel 40 with the heated gas 54 circulating in a counter clockwise direction, or the gas can be circulated clockwise, before the dissipated heat exits through the open top 45 of the lid 44. The heat shield 22, mentioned above, helps protect the operator of from the heat the furnace 10 when holding the handle 28 during its operation.

In this drawing and in operation, the cupel 40 has been heated in a range of 1700 to 1900 degrees F. for a typical period of 30 minutes up to 3 hours. When the assaying of the ore sample 42 is complete, a small bead of gold 56, or other precious metal, is shown left in the bottom of the cupel 40 and after the driving off of sample impurities in the air and absorbed by the cupel. Obviously, this illustration indicates a rare metal is present in the ore sample 42.

Figure 3:
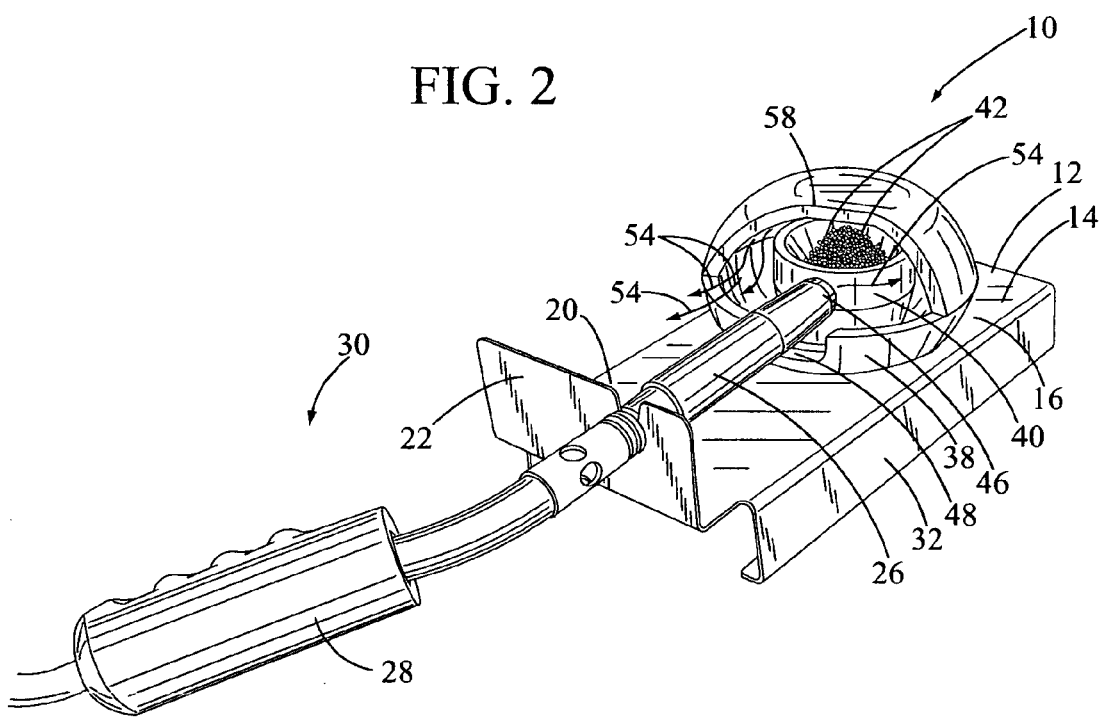
FIG. 3 is another perspective view of the portable furnace shown in FIG. 2. The furnace is shown with a split dish lid rather than a dish lid with opening in its top.

In FIG. 3, another perspective view of the portable furnace 10 is shown and similar to the furnace 10 shown in FIG. 2. In this drawing, the dish lid 44 with open top 45 is replaced with a split lid 58. The split lid 58 is similar in size and shape when compared to the scorifying dish 38 and is similar to one half of the scorifying dish. The split lid 58 is turned upside down and used as shown. As shown in the drawings, the heated exhaust gas 54 exits upwardly and outwardly from the furnace 10 and on the opposite side of the cupel 40 from where the flame 52 is introduced.

While the invention has been particularly shown, described and illustrated in detail with reference to the preferred embodiments and modifications thereof, it should be understood by those skilled in the art that equivalent changes in form and detail may be made therein without departing from the true spirit and scope of the invention as claimed except as precluded by the prior art.

The embodiments of the invention for which as exclusive privilege and property right is claimed are defined as follows:

1. A lightweight furnace used for quickly assaying a crushed ore sample in the field or in the laboratory, the furnace comprising:
   a stand having a stand base with a dish opening therein;
   a scorifying dish, a bottom of the scorifying dish received in the dish opening in the stand base;
   a cupel, the cupel received on top of the scorifying dish, the cupel adapted for receiving a crushed ore sample therein to be assayed;
   a dish lid, the dish lid received on top of the scorifying dish and covering the cupel; and
   gas heat means, the gas heat means for directing a gas flame around an outer circumference of the cupel and heating and assaying the ore sample inside the cupel; wherein the stand is a metal stand and the stand base includes a first end portion with the dish opening therein and a second end portion with an upwardly folded heat shield, the heat shield used to hold a portion of the gas heat means thereon.

2. The furnace as described in claim 1 wherein the gas heat means is a gas blow torch with gas nozzle, a portion of the gas nozzle held on the heat shield, an end of the gas nozzle received inside the scorifying dish and next to the cupel.

3. The furnace as described in claim 2 wherein the scorifying dish includes a dish groove and the dish lid includes a lid groove, the dish groove and the lid groove received around the end of the gas nozzle and for directing a flame from the gas nozzle around the circumference of the cupel.

4. The furnace as described in claim 1 wherein the dish lid includes an open top therein for allowing exhaust gas to escape upwardly from the furnace.

5. The furnace as described in claim 1 wherein the dish lid is cut in half for allowing exhaust gas to escape outwardly and upwardly from the furnace.

6. The furnace as described in claim 1 wherein the stand base includes downwardly extending sides for holding the stand above a flat surface.

7. A lightweight furnace used for quickly assaying a crushed ore sample in the field or laboratory, the furnace comprising:
   a stand having a stand base with a first end portion with a dish opening therein and a second end portion with a heat shield;
   a gas blow torch having a gas nozzle, a portion of the gas nozzle received on the heat shield;
   a scorifying dish, a bottom of the scorifying dish is received in the dish opening in the stand base;
   a cupel, the cupel received on top of the scorifying dish, the cupel adapted for receiving a crushed ore sample therein to be assayed; and
   a dish lid, the dish lid received on top of the scorifying dish, the dish lid used to cover the cupel, the dish lid used to help direct a gas flame from the end of the gas nozzle around an outer circumference of the cupel and heating and assaying the ore sample inside the cupel.

8. The furnace as described in claim 7 wherein the scorifying dish includes a dish groove and the dish lid includes a lid groove, the dish groove and the lid groove received around the end of the gas nozzle for directing the gas flame from the gas nozzle around the circumference of the cupel.

9. The furnace as described in claim 7 wherein the dish lid includes an open top therein for allowing exhaust gas to escape upwardly from the furnace.

10. The furnace as described in claim 7 wherein the dish lid is cut in half for allowing exhaust gas to escape outwardly and upwardly from the furnace.

11. The furnace as described in claim 7 wherein the stand base includes a first side and a second side, the first and second sides folded downwardly and vertically for holding the stand above a flat surface.

12. The furnace as described in claim 7 wherein therein the heat shield includes a nozzle groove therein, a portion of the gas nozzle received inside the nozzle groove.

13. A lightweight furnace used for quickly assaying a crushed ore sample in the field or in the laboratory, the furnace comprising:
- a metal stand having a stand base with a first end portion with a dish opening therein and a second end portion with an upwardly folded heat shield, the heat shield includes a nozzle groove therein;
- a gas blow torch having a gas nozzle, a handle and a gas tank, a portion of the gas nozzle received inside the nozzle groove;
- a scorifying dish, a bottom of the scorifying dish is received in the dish opening in the stand base;
- a cupel, the cupel received on top of the scorifying dish, the cupel adapted for receiving a crushed ore sample therein to be assayed; and
- a dish lid, the dish lid received on top of the scorifying dish, the dish lid used to cover the cupel, the dish lid used to help direct a gas flame from the end of the gas nozzle around an outer circumference of the cupel and heating and assaying the ore sample inside the cupel.

14. The furnace as described in claim 13 wherein the scorifying dish includes a dish groove and the dish lid includes a lid groove, the dish groove and the lid groove received around the end of the gas nozzle and for directing the flame from the gas nozzle around the circumference of the cupel.

15. The furnace as described in claim 13 wherein the dish lid includes an open top therein for allowing exhaust gas to escape upwardly from the furnace.

16. The furnace as described in claim 13 wherein the dish lid is cut in half for allowing exhaust gas to escape outwardly from the furnace.

17. The furnace as described in claim 13 wherein the stand base includes a first side and a second side, the first and second sides folded downwardly and vertically for holding the stand above a flat surface.

* * * * *